United States Patent
Hou et al.

(10) Patent No.: US 12,102,683 B2
(45) Date of Patent: Oct. 1, 2024

(54) PHARMACEUTICAL COMPOSITION OF DILTIAZEM HYDROCHLORIDE, PREPARATION METHOD THEREFOR, AND APPLICATION THEREOF

(71) Applicant: Auson Pharmaceuticals, Inc., Bridgewater, NJ (US)

(72) Inventors: Peng Hou, Shanghai (CN); Enxian Lu, East Brunswick, NJ (US); Longlong Feng, Shanghai (CN)

(73) Assignee: AUSON PHARMACEUTICALS INC., Bridgewater, NJ (US)

( * ) Notice: Subject to any disclaimer, the term of this patent is extended or adjusted under 35 U.S.C. 154(b) by 0 days.

(21) Appl. No.: 18/529,137

(22) Filed: Dec. 5, 2023

(65) Prior Publication Data

US 2024/0108729 A1    Apr. 4, 2024

Related U.S. Application Data

(63) Continuation of application No. PCT/CN2023/074701, filed on Feb. 7, 2023.

(30) Foreign Application Priority Data

Jul. 22, 2022   (CN) .......................... 202210869988X

(51) Int. Cl.
| | |
|---|---|
| *A61K 47/38* | (2006.01) |
| *A61K 9/06* | (2006.01) |
| *A61K 31/554* | (2006.01) |
| *A61K 47/10* | (2017.01) |
| *A61K 47/12* | (2006.01) |
| *A61K 47/32* | (2006.01) |

(52) U.S. Cl.
CPC ................ *A61K 47/38* (2013.01); *A61K 9/06* (2013.01); *A61K 31/554* (2013.01); *A61K 47/10* (2013.01); *A61K 47/12* (2013.01); *A61K 47/32* (2013.01)

(58) Field of Classification Search
None
See application file for complete search history.

(56) References Cited

U.S. PATENT DOCUMENTS 5,019,395 A    5/1991   Mahjour et al.

FOREIGN PATENT DOCUMENTS

| CN | 1515261 A | 7/2004 |
|---|---|---|
| CN | 112020349 A | 12/2020 |
| CN | 115337258 A | 11/2022 |
| EP | 1516622 A1 | 3/2005 |
| WO | 2008022032 A2 | 2/2008 |

OTHER PUBLICATIONS

Cremagel 2% Gel 30gm (available online Jul. 1, 2022). (Year: 2022).*

* cited by examiner

*Primary Examiner* — Melissa S Mercier
(74) *Attorney, Agent, or Firm* — FOX ROTHSCHILD LLP

(57) ABSTRACT

The present invention provides a pharmaceutical composition of diltiazem hydrochloride. The pharmaceutical composition is preferably a gel and consists of diltiazem hydrochloride and excipients including propylene glycol, benzoic acid, and a gel matrix, which is one of or a mixture of povidone and hydroxypropyl cellulose. Based on percentage by weight, the diltiazem hydrochloride accounts for 1%-5%, the benzoic acid accounts for 0.1%-5.0%, the gel matrix accounts for 5%-10%, and the balance is propylene glycol, with pH maintained at 3.0-4.5. A preparation method is provided accordingly, with simple and readily available raw materials and stable quality.

9 Claims, No Drawings

PHARMACEUTICAL COMPOSITION OF DILTIAZEM HYDROCHLORIDE, PREPARATION METHOD THEREFOR, AND APPLICATION THEREOF

TECHNICAL FIELD

The present invention relates particularly to a pharmaceutical composition of diltiazem hydrochloride, a preparation method therefor, and an application thereof, and belongs to the field of pharmaceutical preparations.

BACKGROUND ART

An anal fissure is a small ulcer resulting from the laceration of anal canal skin layer under the dentate line, and often causes severe perianal pain. It is very common in young and middle-aged people, with the typical clinical manifestations of pain, hematochezia, and constipation. The etiology of anal fissure remains unclear, and may be associated with a variety of factors. Most anal fissures are directly caused by mechanical trauma during a bowel movement due to long-term constipation and dried stool. In addition, diarrhea is also one of the important causes of anal fissures. The incidence of anal fissures accounts for about 20% among anorectal diseases.

At present, there are two main therapies for anal fissures, one is drug therapy and the other is surgery (lateral sphincterotomy). However, surgery is often associated with the risk of anal fistula. In order to relieve pain from bowel movements, the drug therapy is the first choice.

The drug therapy includes pain relief therapies, such as lidocaine gel, local injection of botulinum toxin, diltiazem hydrochloride and nitroglycerin cream. Diltiazem hydrochloride also shows a significant effect in the treatment of postoperative pain of hemorrhoids.

Oral tables of diltiazem hydrochloride were first marketed under the trade name Herbesser in Japan in February 1974, with the specifications of 30 mg and 60 mg, and then successively approved by the FDA and EMA, with the maximal specification of 120 mg. The improved new drugs of diltiazem hydrochloride, such as sustained-release capsules (with the maximal specification of 420 mg) and injections (with the maximal specification of 50 mg), were also successively marketed mainly for the treatment of hypertension, angina, and arrhythmia. However, oral administration has shortcomings such as low cure rate and high side effects due to systemic distribution. Hence, the market is in an urgent need of a locally administered preparation of diltiazem hydrochloride with high local concentration and low systemic distribution, such that the side effects of the system can be reduced, and the cure rate can be improved. Marion Jonas et al. conducted a randomized controlled trial of orally and topically administered diltiazem hydrochloride gel. The results showed that the cure rates were 38% and 65%, respectively, and 33% of the orally administered group had side effects such as headache, which might be associated with the systemic plasma concentration resulting from the oral administration, while no side effects were found with the topical administration. Furthermore, the topical administration of diltiazem hydrochloride shows fewer side effects than nitroglycerin cream.

At present, there is no semi-solid dosage form of diltiazem hydrochloride in the market of the United States. The reason lies in that diltiazem hydrochloride is very easily hydrolyzed into deacetyldiltiazem, and the efficacy of this hydrolysate will be reduced by 20%-40%. Moreover, diltiazem hydrochloride is readily oxidized. It is a huge challenge to develop a stable and qualified semi-solid dosage form of diltiazem hydrochloride.

Although semi-solid dosage form of diltiazem hydrochloride is not on the market, its off-label prescriptions have been widely available in retail pharmacies in the United States due to fewer side effects and good efficacy. In 2013, the FDA conducted unannounced inspections in retail pharmacies in the United States and found that 14 of the 36 prescriptions were below the USP standard, and 5 of the 12 pharmacies had an average efficacy lower than 90% of that claimed on the label, which indicate that the diltiazem hydrochloride has a definite efficacy but is difficult to keep stable, this is directly related to the instability of diltiazem hydrochloride in the semi-solid state.

In view of this, this field lacks a semi-solid pharmaceutical composition of diltiazem hydrochloride with simple formulation, readily available excipients, stable quality, reasonable process design, no skin penetration enhancer, and applicability to industrial production.

SUMMARY OF THE INVENTION

In view of the technical problems described above, the present invention provides a pharmaceutical composition of diltiazem hydrochloride, which is preferably a gel and consists of diltiazem hydrochloride and excipients, wherein the excipients include propylene glycol, benzoic acid, and a gel matrix, which is one of or a mixture of povidone and hydroxypropyl cellulose; and based on percentage by weight, the diltiazem hydrochloride accounts for 1%-5%, the benzoic acid accounts for 0.1%-5.0%, the gel matrix accounts for 5%-10%, and the balance is propylene glycol.

In a preparation of the present invention, the prepared gel has pH maintained at 3.0-4.5.

According to the pharmaceutical composition of the present invention, a resultant product does not contain water. This is completely different from the conventional water-soluble gel. The technical problem to be solved is how to obtain a stable pharmaceutical composition capable of withstanding a variety of extreme environments.

Further preferably, in the pharmaceutical composition described above, based on percentage by weight, the diltiazem hydrochloride accounts for 1%-5%, the benzoic acid accounts for 0.1%-3.0%, the gel matrix accounts for 5.0%-9.0%, and the balance is propylene glycol.

Further preferably, in the pharmaceutical composition described above, based on percentage by weight, the diltiazem hydrochloride accounts for 1%-4%, the benzoic acid accounts for 0.1%-2.0%, the gel matrix accounts for 7.0%-9.0%, and the balance is propylene glycol.

Further preferably, in the pharmaceutical composition described above, based on percentage by weight, the diltiazem hydrochloride accounts for 1%-4%, the benzoic acid accounts for 0.1%-1.0%, the gel matrix accounts for 7.0%-9.0%, and the balance is propylene glycol.

Further preferably, in the pharmaceutical composition described above, based on percentage by weight, the diltiazem hydrochloride accounts for 1%-4%, the benzoic acid accounts for 0.25%-0.75%, the gel matrix accounts for 7.0%-9.0%, and the balance is propylene glycol.

Further preferably, in the pharmaceutical composition described above, the gel matrix is hydroxypropyl cellulose.

Further preferably, in the pharmaceutical composition described above, the diltiazem hydrochloride accounts for 2% by weight.

Further preferably, in the pharmaceutical composition described above, the pharmaceutical composition consists of 2% of the diltiazem hydrochloride, 89.5% of the propylene glycol, 0.5% of the benzoic acid, and 8.0% of the hydroxypropyl cellulose.

The present invention further provides a preparation method for the pharmaceutical composition described above, including the following steps:
1) mixing propylene glycol accounting for 35%-70% of a prescribed amount with a gel matrix, stirring a resulting mixture for emulsification to obtain a matrix A;
2) mixing a prescribed amount of benzoic acid with the balance of propylene glycol, and stirring a resulting mixture to obtain a solution B;
3) adding a prescribed amount of diltiazem hydrochloride to the solution B, stirring and heating a resulting mixture for dissolution to obtain a solution C; and
4) adding the solution C to the matrix A for overall mixing in a homogeneous and uniform manner, and cooling a resulting mixture to room temperature to obtain the pharmaceutical composition.

The present invention further provides an application of the pharmaceutical composition described above to preparation of drugs for treatment of anal fissures and postoperative pain of anal fissures or hemorrhoids.

The preparation method may specifically include the followings:

i Preparation of Gel Matrix of Hydroxypropyl Cellulose LXF

Propylene glycol is weighed out for later use; part of propylene glycol (35-70% of the prescribed amount) is poured into an emulsification pot; stirring is started; under a stirring state at a speed of 30-50 rpm, the prescribed amount of hydroxypropyl cellulose LXF is slowly added to the emulsification pot by vacuum pumping within no less than 5 minutes; a resulting mixture is stirred until complete and even dispersion; then, the mixture is heated 70-80° C. to allow swelling of the gel matrix into transparency at a stirring speed of 30-50 rpm; and after full swelling, the matrix is cooled to 40-55° C. for later use.

ii Dissolution of Benzoic Acid

The remaining part of propylene glycol is poured into an oil phase pot; and benzoic acid is weighed and added to the oil phase pot, and then stirred and heated for dissolution, with a stirring speed of 40-55 rpm, a heating temperature of 40-50° C., and a stirring duration of 10-60 min.

iii Dissolution of Diltiazem Hydrochloride

Diltiazem hydrochloride is weighed and poured to the oil phase pot, and then stirred and heated till complete dissolution, with a stirring speed of 40-55 rpm, a heating temperature of 40-50° C., and a stirring duration of 20-30 min.

iv Overall Mixing

With the stirring speed (40-55 rpm) and temperature of the emulsification pot unchanged, a solution in the oil phase pot is added to the emulsification pot by vacuum pumping; with the emulsification pot in a vacuum state of 0.05--0.10 MPa, materials in the emulsification pot are stirred and homogenized for 30-60 min at a rotating speed of 40-55 rpm and a homogenization speed of 40-55 rpm to allow even mixing of the materials; and finally, the materials are cooled to room temperature to obtain the composition as described.

The technical effect to be achieved by the present invention is:
1. the pharmaceutical composition is preferably a gel, which, due to its transparency, has better acceptability than creams and ointments and does not contain an oil phase, thus without phase separation.
2. The present invention conforms to more stringent quality control standards.

According to USP, diltiazem hydrochloride tablets should have a content accounting for 93.0%-107.0% of the labeled content, with any individual impurity ≤0.5%. If the content is out of this range, decreased efficacy may be caused, and if any individual impurity is too high in content, toxicity and even cancer may be caused after long-term use. Accordingly, International Conference on Harmonization of Requirements for Registration Pharmaceuticals for Human Use (ICH) published the document Q3B to strictly control the single impurities in prepared drug products (single impurity≤0.2%). In order to develop a gel with superior quality and safety, the development objective of the present patent is to control the content of diltiazem hydrochloride at 95.0%-105.0%, and any individual impurity ≤0.2%, and the internal control standards are stricter than those in the USP, which further prevents the risk of reduced efficacy of active ingredients in a later stage.

In another aspect, the diltiazem hydrochloride contains an ester bond and is easily hydrolyzed into deacetyldiltiazem (Imp-F), which is an in vivo metabolite with recognized safety. However, the activity of the hydrolysate deacetyldiltiazem (Imp-F) is 20%-40% of the activity of diltiazem hydrochloride. Considering that the minimum content of diltiazem hydrochloride is 95.0% under internal control, Imp-F is controlled to be ≤3.0% in the present patent.

Therefore, the objective of formulation development of the present patent is: single impurity≤0.2%; Imp-F≤3.0%; and total impurities≤3.0%. The content of total impurities is controlled.

The development difficulty of the present patent lies in the following four aspects.
1. Diltiazem hydrochloride is extremely unstable and prone to hydrolysis and oxidation, which will be accelerated in water, and thus the formulation cannot include water.
2. An appropriate solvent capable of dissolving a thickener and the diltiazem hydrochloride therein needs to be selected, and the diltiazem hydrochloride should keep stable in this solvent.
3. An appropriate preservative and/or pH regulator need(s) to be selected to increase the stability of the preparation.
4. Since the diltiazem hydrochloride is prone to oxidation, an antioxidant may be added to the formulation, and the antioxidant is also soluble in the solvent. The diltiazem hydrochloride, thickening matrix, pH regulator, and antioxidant must be dissolved in the solvent, and the prepared product must be stable, both of which bring severe challenges to the development of the preparation. By means of gradual optimization, the inventor finally obtains the target formulation of the present patent.

In view of the first development difficulty described above, no water should be contained in the formulation. It means that organic solvent is needed while the concentration of diltiazem should be kept unchanged. At this point, a variety of solvents need to be added, which may lead to stability and compatibility problems among these solvents. The inventor conducted mono-component and multi-component mixing of propylene glycol, glycerin, and polyethylene glycol, to finally screen out the propylene glycol at the concentration of greater than 80% for better stability of the formulation, as described in Example 1 (formulation 5 in Table 1).

In view of the second development difficulty described above, an appropriate thickener is required. The inventor conducted many experiments to finally determine that povidone K90 and hydroxypropyl methylcellulose LXF meet the requirements as thickeners, and hydroxypropyl methylcellulose LXF is relatively superior, as described in Example 2 (formulations 5 and 10 in Table 4).

In view of the third development difficulty described above, the inventor conducted a study on preservatives (ethylparaben, benzyl alcohol and benzoic acid) compatible with propylene glycol, and screened out a benzoic acid-containing formulation (formulation 12) with greatly improved stability, which was speculated to be due to the pH regulation effect of benzoic acid. Then, a control test taking hydrochloric acid as a pH regulator was designed. It was found that the benzoic acid-containing formulation was superior to that containing hydrochloric acid (Table 9). Therefore, the benzoic acid contributes to the formulation of the present patent not only in terms of preservatives, but also in the synergistic effect of pH regulation and antiseptic. Afterwards, the inventor conducted in-depth studies on different contents of benzoic acid, and found that the benzoic acid with the content of 0.25%-0.75% met the development objective (particularly in stability) of the present patent, as shown in Table 12.

In view of the fourth development difficulty described above, because no water is contained in the present patent, the oxidation reaction is very weak. In order to develop the optimal formulation, the inventor also conducted researches on different antioxidants, and found that butylhydroxyanisole (BHA) and dl-α-tocopherol showed similar antioxidant effects at room temperature, and dl-α-tocopherol was slightly superior at high temperature of 60° C. Furthermore, the effects of different contents of dl-α-tocopherol on the stability of the preparation were investigated. It was found that 0.02%-0.5% DL-α-tocopherol had no significant effect on the stability of the preparation under refrigeration and at room temperature, but significantly improved the stability of the preparation at high temperature of 60° C. (Table 16).

The developed formulation of the present patent has the following 5 characteristics.
1. No water is contained in the formulation, which improves the stability of diltiazem hydrochloride.
2. Propylene glycol as the solvent of the gel generally has a content of not more than 20%, and the amount of propylene glycol (>80%) used in the present patent is much greater than the general amount, which improves product stability. Furthermore, the maximum daily use of Propylene glycol in the present product is less than 3000 mg, which is far below the FDA approved maximum dosage of 6113 mg for topical administration.
3. Benzoic acid shows a unique property in the present formulation, which greatly improves the stability of the formulation of the present patent.
4. The dosage form of gel is transparent in appearance, which increases patient acceptability as compared with creams and ointments, and the gel has no oil phase and no phase separation.
5. The gel of the present patent has a shelf life of at least 1 year at room temperature or under refrigeration.

DETAILED DESCRIPTION OF THE PREFERRED EMBODIMENTS

The embodiments below are merely intended to further illustrate the present invention but are not intended to limit the present invention. All techniques implemented based on the above description of the present invention shall be construed as falling within the scope of the present invention.

According to the literatures, 2% diltiazem hydrochloride at 3 times/day and 1 g/time has demonstrated the effectiveness. Therefore, diltiazem hydrochloride at the concentration of 2% is used in the formulation screening.

In the screening experiment of the present invention, the preparation method described in Example 7 is used, and the reagents of the same class are added sequentially.

Example 1— Selection of Different Solvents

In order to allow the diltiazem hydrochloride in a dissolved state in a gel matrix, the applicant first investigated the solubility of the diltiazem hydrochloride in propylene glycol, glycerin, and polyethylene glycol, of which propylene glycol showed the highest solubility up to 79 mg/ml. Therefore, propylene glycol was used as a basic solvent in the formulation of the present patent.

Propylene glycol has been widely used in gel preparations, with the common usage level not exceeding 20%. Considering that the present patent involved an anhydrous gel and required an additional solvent for supplement, the present inventor investigated the effect of propylene glycol on the stability of diltiazem by taking propylene glycol as a basic solvent, glycerin and polyethylene glycol as solvent supplements, ethylparaben as a preservative, and povidone as a gel matrix. The compositions of formulations are shown in the table below. Because an anhydrous solvent is to be used, none of the existing anhydrous solvents is used at a level of more than 20%. However, there is no clear usage guidance on whether more than 20% of a single solvent is better or whether it is necessary to mix different solvents, in the present invention. In addition, it has been found that even if high-concentration propylene glycol is used, the safety and effectiveness in the later stage are not affected.

TABLE 1

Investigation of different solvents

| Compositions of formulations | Formulation 1 | Formulation 2 | Formulation 3 | Formulation 4 | Formulation 5 |
|---|---|---|---|---|---|
| Diltiazem hydrochloride | 2 g | 2 g | 2 g | 2 g | 2 g |
| Propylene glycol | 20 g | 50 g | 80 g | 80 g | 89.75 g |
| Glycerin | 30 g | 20 g | 9.75 g | — | — |
| Polyethylene glycol | 39.75 g | 19.75 g | — | 9.75 g | — |
| Ethylparaben | 0.25 g | 0.25 g | 0.25 g | 0.25 g | 0.25 g |
| Povidone K90 | 8 g | 8 g | 8 g | 8 g | 8 g |
| Total weight | 100 g | 100 g | 100 g | 100 g | 100 g |

Appearance, viscosity, and skin feel are evaluated as shown in the table below.

TABLE 2

Evaluation of formulations with different solvents

| Evaluation Endpoints | Formulation 1 | Formulation 2 | Formulation 3 | Formulation 4 | Formulation 5 |
|---|---|---|---|---|---|
| Appearance | Transparent and homogeneous | Transparent and homogeneous | Transparent and homogeneous | Transparent and homogeneous | Transparent and homogeneous |
| Viscosity | 17445 cp | 18335 cp | 25090 cp | 15433 cp | 18160 cp |
| Skin feel evaluation | Moderate viscosity | Moderate viscosity | High viscosity | Moderate viscosity | Moderate viscosity |

Stability is evaluated as shown in the table below.

TABLE 3

| Storage condition and time | Formulation 1 | Formulation 2 | Formulation 3 | Formulation 4 | Formulation 5 |
|---|---|---|---|---|---|
| 0 day | Single impurity: ND Imp-F: 0.25% Total impurities: 0.25% | Single impurity: ND Imp-F: 0.26% Total impurities: 0.26% | Single impurity: ND Imp-F: 0.27% Total impurities: 0.27% | Single impurity: ND Imp-F: 0.25% Total impurities: 0.25% | Single impurity: ND Imp-F: 0.27% Total impurities: 0.27% |
| Cold storage (2-8° C.), 1M | Single impurity: 0.31% Imp-F: 0.77% Total impurities: 1.08% | Single impurity: 0.26% Imp-F: 0.70% Total impurities: 0.96% | Single impurity: 0.16% Imp-F: 0.63% Total impurities: 0.79% | Single impurity: 0.18% Imp-F: 0.67% Total impurities: 0.85% | Single impurity: 0.16% Imp-F: 0.57% Total impurities: 0.73% |
| 25°C/60% RH, 1M (room temperature) | Single impurity: 1.23% Imp-F: 2.33% Total impurities: 3.56% | Single impurity: 0.93% Imp-F: 1.94% Total impurities: 2.87% | Single impurity: 0.35% Imp-F: 1.31% Total impurities: 1.66% | Single impurity: 0.40% Imp-F: 1.44% Total impurities: 1.84% | Single impurity: 0.35% Imp-F: 1.11% Total impurities: 1.46% |
| 40°C/75% RH, 1M | Single impurity: 3.01% Imp-F: 6.34% Total impurities: 9.35% | Single impurity: 2.88% Imp-F: 5.98% Total impurities: 8.86% | Single impurity: 1.99% Imp-F: 4.05% Total impurities: 6.04% | Single impurity: 3.50% Imp-F: 4.42% Total impurities: 7.92% | Single impurity: 1.97% Imp-F: 3.27% Total impurities: 5.24% |

ND: not detected; LOQ: 0.05%, the same below.

Conclusion: The above data show that with the propylene glycol, glycerin, and polyethylene glycol as solvents, the formulation containing polyethylene glycol shows the worst stability, the formulation containing glycerin comes second, and the formulation containing propylene glycol shows the best stability. Better stability is achieved when the content of the propylene glycol is greater than 80%, but when this formulation (formulation 5) is stored for 1 M at room temperature, the single impurity content of 0.35% is higher than the internal control standard of 0.2% and does not meet the requirements. Therefore, it is necessary to continue to optimize this formulation.

Example 2—Selection of Different Thickeners

In Example 1, we have screened propylene glycol for optimal stability relative to glycerin and polyethylene glycol. In this test, the thickener is optimized based on the formulation 5. Since different thickeners differ in viscosity, the content of thickener in the formulation may be different in the context of ensuring moderate viscosity, but will not affect the conclusion of the study. Thickeners such as carbopol, hydroxypropyl methylcellulose (HPMC), sodium carboxymethylcellulose (CMC-Na), povidone PVP K90, and hydroxypropyl cellulose (HPC) were screened. The compositions of formulations are shown in the table below.

TABLE 4

Compositions of formulations with different thickeners

| Compositions of formulations | Formulation 5 PVP K90 | Formulation 6 Carbopol | Formulation 7 HPMC | Formulation 8 CMC-Na | Formulation 10 HPC |
|---|---|---|---|---|---|
| Diltiazem hydrochloride | 2 g | 2 g | 2 g | 2 g | 2 g |
| Propylene glycol | 89.75 g | 95.75 g | 91.75 g | 94.75 g | 89.75 g |
| Ethylparaben | 0.25 g | 0.25 g | 0.25 g | 0.25 g | 0.25 g |
| Povidone K90 | 8 g | — | — | — | — |
| Carbomer 971 | — | 2 g | — | — | — |
| Hydroxypropyl methylcellulose K4M | — | — | 6 g | — | — |

TABLE 4-continued

Compositions of formulations with different thickeners

| Compositions of formulations | Formulation 5 PVP K90 | Formulation 6 Carbopol | Formulation 7 HPMC | Formulation 8 CMC-Na | Formulation 10 HPC |
|---|---|---|---|---|---|
| Sodium carboxymethyl-cellulose VIVASOL | — | — | — | 3 g | — |
| Hydroxypropyl cellulose LXF | — | — | — | — | 8 g |
| Total weight | 100 g | 100 g | 100 g | 100 g | 100 g |

Appearance, viscosity, and skin feel are evaluated as shown in the table below.

TABLE 5

Evaluation of formulations with different thickeners

| Evaluation Endpoints | Formulation 5 PVP K90 | Formulation 6 Carbopol | Formulation 7 HPMC | Formulation 8 CMC-Na | Formulation 10 HPC |
|---|---|---|---|---|---|
| Appearance | Transparent and homogeneous | Dissolved, rough | Undissolved | Undissolved | Transparent and homogeneous |
| Viscosity | 18160 cp | 12000 cp | ND | ND | 13310 cp |
| Skin feel evaluation | Moderate viscosity | ND | ND | ND | Moderate viscosity |

Conclusion: the carbopol was soluble in propylene glycol, but with rough appearance, and the viscosity and skin feel were no longer evaluated; the hydroxypropyl methylcellulose and the sodium carboxymethylcellulose were insoluble in propylene glycol, and the viscosity and skin feel were no longer evaluated; and the formulation 5 and formulation 10 showed a transparent and homogenous appearance with moderate viscosity, and thus are evaluated in stability, as shown in the table below.

TABLE 6

Stability results of formulation 5 and formulation 10

| Storage condition and time | Formulation 5 PVP K90 | Formulation 10 HPC |
|---|---|---|
| 0 day | Single impurity: ND<br>Imp-F: 0.27%<br>Total impurities: 0.27% | Single impurity: <LOQ<br>Imp-F: 0.07%<br>Total impurities: 0.07% |
| Cold storage (2-8° C.), 1M | Single impurity: 0.16%<br>Imp-F: 0.57%<br>Total impurities: 0.73% | Single impurity: 0.11%<br>Imp-F: 0.22%<br>Total impurities: 0.33% |
| 25°C/60% RH, 1M (room temperature) | Single impurity: 0.35%<br>Imp-F: 1.11%<br>Total impurities: 1.46% | Single impurity: 0.26%<br>Imp-F: 0.75%<br>Total impurities: 1.01% |
| 40°C/75% RH, 1M | Single impurity: 1.97%<br>Imp-F: 3.27%<br>Total impurities: 5.24% | Single impurity: 1.27%<br>Imp-F: 3.05%<br>Total impurities: 4.32% |

Conclusion: hydroxypropyl cellulose (HPC) as the thickening matrix of the gel showed better stability than that of povidone (PVP K90) as the thickening matrix. However, after storage for 1 M at room temperature (25° C./60% RH humidity), the single impurity accounted for 0.26% which was greater than the internal control standard of 0.2%. Therefore, it was necessary to continue to optimize this formulation.

Since both the solvent and the thickener had been determined, the appearance and skin feel of the gel were no longer evaluated in the following investigation, which mainly focused on stability optimization.

Example 3— Screening Among Different Preservatives

Example 2 demonstrates that the formulation taking the propylene glycol as a solvent and the hydroxypropyl cellulose as a thickener show the best stability, but with the single impurity content that is still greater than the internal control standard of 0.2%. Hence, this test investigates the effects of different preservatives. We selected two additional preservatives, namely, benzyl alcohol and benzoic acid, for a contrast test, and the formulation compositions were shown in the table below.

TABLE 7

Screening of different preservative types

| Compositions of formulations | Formulation 10 0.25% of ethylparaben | Formulation 11 0.25% of benzyl alcohol | Formulation 12 0.25% of benzoic acid |
|---|---|---|---|
| Diltiazem hydrochloride | 2 g | 2 g | 2 g |
| Propylene glycol | 89.75 g | 89.75 g | 89.75 g |
| Ethylparaben | 0.25 g | — | — |
| Benzyl alcohol | — | — | — |
| Benzoic acid | — | — | 0.25 g |
| Hydroxypropyl cellulose | 8 g | 8 g | 8 g |
| Total weight | 100 g | 100 g | 100 g |

Stability is evaluated as shown in the table below.

TABLE 8

Stability results for different preservatives

| Storage condition and time | Formulation 10 0.25% of ethylparaben | Formulation 11 0.25% of benzyl alcohol | Formulation 12 0.25% of benzoic acid |
|---|---|---|---|
| 0 day | Single impurity: <LOQ<br>Imp-F: 0.07%<br>Total impurities: 0.07% | Single impurity: <LOQ<br>Imp-F: 0.06%<br>Total impurities: 0.06% | Single impurity: <LOQ<br>Imp-F: < LOQ<br>Total impurities: <LOQ |

TABLE 8-continued

Stability results for different preservatives

| Storage condition and time | Formulation 10 0.25% of ethylparaben | Formulation 11 0.25% of benzyl alcohol | Formulation 12 0.25% of benzoic acid |
|---|---|---|---|
| Cold storage (2-8° C.), 1M | Single impurity: 0.11% Imp-F: 0.22% Total impurities: 0.33% | Single impurity: 0.13% Imp-F: 0.24% Total impurities: 0.37% | Single impurity: <LOQ Imp-F: 0.06% Total impurities: 0.06% |
| 25°C/60% RH, 1M (room temperature) | Single impurity: 0.26% Imp-F: 0.75% Total impurities: 1.01% | Single impurity: 0.25% Imp-F: 0.70% Total impurities: 0.95% | Single impurity: 0.06% Imp-F: 0.24% Total impurities: 0.30% |

Conclusion: after the investigations on different types of preservatives, we were surprised to find that formulations containing benzoic acid were far more stable than formulations containing ethylparaben and benzyl alcohol. After storage for 1 M at room temperature (25° C./60% RH humidity), the single impurity accounted for 0.06% which was less than the internal control standard of 0.2%, and the hydrolyzed impurity Imp-F accounted for 0.24%, which was far less than the internal control standard of 3.0%. It was speculated that benzoic acid reduced the pH of the gel, which improved the stability of the preparation. Next, the stability of the preparations of the present patent was investigated with respect to other pH regulators, and the compositions of formulations was shown in the table below.

TABLE 9

Compositions of formulations different pH regulators

| Compositions of formulations | Formulation 12 0.25% of benzoic acid | Formulation 13 Hydrochloric acid/sodium hydroxide |
|---|---|---|
| Diltiazem hydrochloride | 2 g | 2 g |
| Propylene glycol | 89.75 g | 89.75 g |
| Benzoic acid | 0.25 g | — |
| Hydrochloric acid/sodium hydroxide | — | Regulate to target pH |
| Hydroxypropyl cellulose | 8 g | 8 g |
| Total weight | 100 g | 100 g |

Conclusion: since citric acid and sodium dihydrogen phosphate were insoluble in propylene glycol, hydrochloric acid was selected for a contrast study. The pH value and stability of each formulation studied were shown in the table below.

TABLE 10

Stability results for different pH regulators

| Storage condition and time | Formulation 12 0.25% of benzoic acid | Formulation 13 Hydrochloric acid/sodium hydroxide |
|---|---|---|
| pH value of gel 0 day | 3.8 Single impurity: <LOQ Imp-F: <LOQ Total impurities: <LOQ | 3.8 Single impurity: <LOQ Imp-F: 0.06% Total impurities: 0.06% |

TABLE 10-continued

Stability results for different pH regulators

| Storage condition and time | Formulation 12 0.25% of benzoic acid | Formulation 13 Hydrochloric acid/sodium hydroxide |
|---|---|---|
| Cold storage (2-8° C.), 1M | Single impurity: <LOQ Imp-F: 0.06% Total impurities: 0.06% | Single impurity: 0.23% Imp-F: 0.86% Total impurities: 1.09% |
| 25° C./60% RH, 1M (room temperature) | Single impurity: 0.06% Imp-F: 0.24% Total impurities: 0.30% | Single impurity: 0.44% Imp-F: 2.14% Total impurities: 2.58% |

Conclusion: we found that hydrochloric acid as the most conventional pH regulator did not meet relevant preparation requirements. The formulation with Benzoic acid showed better stability than that with hydrochloric acid. Hence, the stability of the formulation 12 was improved not only due to the pH-regulating performance of benzoic acid, but also due to the synergistic effect of antiseptic. The unique characteristics of benzoic acid greatly improved the stability of the formulation of the present patent.

Example 4—Screening of Different Contents of Benzoic Acid

Example 3 has demonstrated that the unique characteristics of benzoic acid greatly improves the stability of the formulation of the present patent. The content of benzoic acid is investigated in this test. In order to quickly screen out the optimal formulation, the investigation was carried out after storage for 1 week at the high temperature of 60° C. The compositions of formulations were shown in the table below.

TABLE 11

Compositions of formulations with different contents of benzoic acid

| Compositions of formulations | Formulation 12 0.25% of benzoic acid | Formulation 14 0.5% of benzoic acid | Formulation 15 0.75% of benzoic acid |
|---|---|---|---|
| Diltiazem hydrochloride | 2 g | 2 g | 2 g |
| Propylene glycol | 89.75 g | 89.50 g | 89.25 g |
| Benzoic acid | 0.25 g | 0.5 g | 0.75 g |
| Hydroxypropyl cellulose | 8 g | 8 g | 8 g |
| Total weight | 100 g | 100 g | 100 g |

Stability is evaluated as shown in the table below.

TABLE 12

Summary of stability of formulations with different contents of benzoic acid

| Storage condition and time | Formulation 12 0.25% of benzoic acid | Formulation 14 0.5% of benzoic acid | Formulation 15 0.75% of benzoic acid |
|---|---|---|---|
| pH value of gel | 3.8 | 3.4 | 3.4 |
| 0 day | Single impurity: <LOQ<br>Imp-F: < LOQ<br>Total impurities: <LOQ | Single impurity: <LOQ<br>Imp-F: <LOQ<br>Total impurities: <LOQ | Single impurity: <LOQ<br>Imp-F: <LOQ<br>Total impurities: <LOQ |
| Cold storage (2-8° C.), 3M | Single impurity: <LOQ<br>Imp-F: 0.17%<br>Total impurities: 0.17% | Single impurity: <LOQ<br>Imp-F: 0.13%<br>Total impurities: 0.13% | Single impurity: <LOQ<br>Imp-F: 0.14%<br>Total impurities: 0.14% |
| 25°C/60% RH, 3M (room temperature) | Single impurity: 0.08%<br>Imp-F: 0.83%<br>Total impurities: 0.91% | Single impurity: 0.05%<br>Imp-F: 0.62%<br>Total impurities: 0.67% | Single impurity: <LOQ<br>Imp-F: 0.62%<br>Total impurities: 0.62% |
| Storage condition and time | Formulation 12 0.25% of benzoic acid | Formulation 14 0.5% of benzoic acid | Formulation 15 0.75% of benzoic acid |
| Hight temperature of 60° C., 1 week | Single impurity: 0.15%<br>Imp-F: 1.75%<br>Total impurities: 1.90% | Single impurity: 0.14%<br>Imp-F: 1.67%<br>Total impurities: 1.81% | Single impurity: 0.15%<br>Imp-F: 1.65%<br>Total impurities: 1.80% |
| Hight temperature of 60° C., 2 weeks | Single impurity: 0.44%<br>Imp-F: 4.23%<br>Total impurities: 4.67% | Single impurity: 0.39%<br>Imp-F: 3.99%<br>Total impurities: 4.38% | Single impurity: 0.41%<br>Imp-F: 4.04%<br>Total impurities: 4.45% |

Conclusion: all the formulations with 0.25%-0.75% of benzoic acid met the internal control standards (single impurity≤0.2%, Imp-F≤3.0%) after storage for 3 months at room temperature. According to the growth trend of impurities, the formulations 12, 14 and 15 could be stored for at least 2 years under refrigerated conditions, and at least 1 year under room temperature conditions, all of which met the development objective of the present patent. In order to allow the optimal formulation developed by the present patent, considering that both single impurities and Imp-F significantly increased under high temperature conditions, the effect of antioxidants was investigated on the basis of the formulation 14 in the next step.

Example 5—Screening of Different Antioxidant Types

The addition of antioxidants to the formulation could improve the oxidation of diltiazem. In order to further improve the stability of the preparation, the present patent investigated the effects of butyl hydroxyanisole (BHA), dibutylhydroxytoluene (BHT) and DL-α-tocopherol on the stability of the preparation. The compositions of formulations were shown in the table below.

TABLE 13

Compositions of formulations with different antioxidant types

| Compositions of formulations | Formulation 16 0.02% BHT | Formulation 17 0.02% BHA | Formulation 18 0.02% of DL-α-tocopherol |
|---|---|---|---|
| Diltiazem hydrochloride | 2 g | 2 g | 2 g |
| Propylene glycol | 89.48 g | 89.48 g | 89.48 g |
| Benzoic acid | 0.5 g | 0.5 g | 0.5 g |
| Dibutylhydroxytoluene (BHT) | 0.02 g | — | — |
| Butylhydroxyanisole (BHA) | — | 0.02 g | — |
| DL-α-tocopherol | — | — | 0.02 g |
| Hydroxypropyl cellulose | 8 g | 8 g | 8 g |
| Total weight | 100 g | 100 g | 100 g |

BHT was insoluble in propylene glycol and thus was no longer subject to stability investigation.

The stability achieved by taking BHA and DL-α-tocopherol as antioxidants was evaluated as shown in the table below.

TABLE 14

Stability results for different antioxidant types

| Storage condition and time | Formulation 17 0.02% BHA | Formulation 18 0.02% of DL-α-tocopherol |
|---|---|---|
| 0 day | Single impurity: <LOQ<br>Imp-F: 0.08%<br>Total impurities: 0.08% | Single impurity: <LOQ<br>Imp-F: 0.07%<br>Total impurities: 0.07% |

TABLE 14-continued

Stability results for different antioxidant types

| Storage condition and time | Formulation 17 0.02% BHA | Formulation 18 0.02% of DL-α-tocopherol |
|---|---|---|
| Cold storage (2-8° C.), 1M | Single impurity: 0.05% Imp-F: 0.08% Total impurities: 0.13% | Single impurity: <LOQ Imp-F: 0.10% Total impurities: 0.10% |
| 25°C/60% RH, 1M (room temperature) | Single impurity: 0.10% Imp-F: 0.23% Total impurities: 0.33% | Single impurity: <LOQ Imp-F: 0.25% Total impurities: 0.25% |
| Hight temperature of 60° C., 2 weeks | Single impurity: 0.30% Imp-F: 3.88% Total impurities: 4.18% | Single impurity: 0.26% Imp-F: 3.71% Total impurities: 3.97% |

Conclusion: DL-α-tocopherol as the antioxidant was slightly superior to BHA. Next, the effect of different amounts of the antioxidant on the stability of the preparation was investigated.

Example 6—Screening of the Amounts of DL-α-Tocopherol as Antioxidant

DL-α-tocopherol as an antioxidant had been demonstrated to be superior to BHA. The objective this test was to screen for an appropriate amount. The compositions of formulations were shown in the table below.

TABLE 15

Compositions of formulations with different vitamins E

| Compositions of formulations | Formulation 18 0.02% of DL-α-tocopherol | Formulation 19 0.1% of DL-α-tocopherol | Formulation 20 0.25% of DL-α-tocopherol | Formulation 21 0.5% of DL-α-tocopherol |
|---|---|---|---|---|
| Diltiazem hydrochloride | 2 g | 2 g | 2 g | 2 g |
| Propylene glycol | 89.48 g | 89.4 g | 89.25 g | 89.00 g |
| Benzoic acid | 0.5 g | 0.5 g | 0.5 g | 0.5 g |
| Vitamin E | 0.02 g | 0.1 g | 0.25 g | 0.5 g |
| Hydroxypropyl cellulose | 8 g | 8 g | 8 g | 8 g |
| Total weight | 100 g | 100 g | 100 g | 100 g |

Stability is summarized in the table below.

TABLE 16

Summary of stability of formulations with different DL-α-tocopherol

| Storage condition and time | Formulation 18 0.02% of DL-α-tocopherol | Formulation 19 0.1% of DL-α-tocopherol | Formulation 20 0.25% of DL-α-tocopherol | Formulation 21 0.5% of DL-α-tocopherol |
|---|---|---|---|---|
| 0 day | Single impurity: <LOQ Imp-F: 0.07% Total impurities: 0.07% | Single impurity: <LOQ Imp-F: 0.07% Total impurities: 0.07% | Single impurity: <LOQ Imp-F: 0.07% Total impurities: 0.07% | Single impurity: <LOQ Imp-F: 0.07% Total impurities: 0.07% |
| Cold storage (2-8° C.), 1M | Single impurity: <LOQ Imp-F: 0.10% Total impurities: 0.10% | Single impurity: <LOQ Imp-F: 0.11% Total impurities: 0.11% | Single impurity: <LOQ Imp-F: 0.11% Total impurities: 0.11% | Single impurity: <LOQ Imp-F: 0.11% Total impurities: 0.11% |
| 25° C./60% RH, 1M (room temperature) | Single impurity: <LOQ Imp-F: 0.25% Total impurities: 0.25% | Single impurity: <LOQ Imp-F: 0.27% Total impurities: 0.27% | Single impurity: <LOQ Imp-F: 0.29% Total impurities: 0.29% | Single impurity: <LOQ Imp-F: 0.27% Total impurities: 0.27% |
| High temperature of 60° C., 15 days | Single impurity: 0.26% Imp-F: 3.71% Total impurities: 3.97% | Single impurity: 0.18% Imp-F: 3.51% Total impurities: 3.69% | Single impurity: 0.08% Imp-F: 3.35% Total impurities: 3.43% | Single impurity: 0.06% Imp-F: 3.25% Total impurities: 3.31% |

Conclusion: 0.02%-0.5% of DL-α-tocopherol showed no significant effect on the stability of the preparation under refrigeration and at room temperature, but could improve the stability of the preparation at the high temperature of 60° C.

Example 7

The formulation confirmed by the small test was scaled up to 30 kg, and the composition of the formulation was shown in the table below.

TABLE 17

Composition of scaled-up formulation (lot size: 30 kg)

| Compositions of formulations | 2% (w/w) Kg/lot | Percentage %, w/w |
|---|---|---|
| Diltiazem hydrochloride | 0.6 | 2 |
| Propylene glycol | 26.85 | 89.5 |
| Benzoic acid | 0.15 | 0.5 |
| Hydroxypropyl cellulose | 2.4 | 8 |
| Total weight | 30 | 100 |

The process was as follows.

i Preparation of Gel Matrix of Hydroxypropyl Cellulose LXF

Propylene glycol was weighed out for later use; the propylene glycol (60% of the prescribed amount) was poured into an emulsification pot; stirring was started; under a stirring state at a speed of 30-50 rpm, the prescribed amount of hydroxypropyl cellulose LXF was slowly added to the emulsification pot by vacuum pumping within no less than 5 minutes; a resulting mixture was stirred till complete and even dispersion; then, the mixture was heated to 70-80° C. to allow swelling of the gel matrix into transparency at a stirring speed of 30-50 rpm; and after full swelling, the matrix was cooled to 55° C. for later use.

ii Dissolution of Benzoic Acid

The remaining part of propylene glycol was poured into an oil phase pot; and benzoic acid was weighed and added to the oil phase pot, and then stirred and heated for dissolution, with a stirring speed of 50 rpm, a heating temperature of 50° C., and a stirring duration of 30 min.

iii Dissolution of Diltiazem Hydrochloride

Diltiazem hydrochloride was weighed and poured to the oil phase pot, and then stirred and heated till complete dissolution, with a stirring speed of 50 rpm, a heating temperature of 50° C., and a stirring duration of 30 min.

iv Overall Mixing

With the stirring speed (50 rpm) and temperature of the emulsification pot unchanged, a solution in the oil phase pot was added to the emulsification pot by vacuum pumping; with the emulsification pot in a vacuum state of 0.05--0.10 MPa, materials in the emulsification pot were stirred and homogenized for 60 min at a rotating speed of 50 rpm and a homogenization speed of 45 rpm to allow even mixing of the materials; and finally, the materials were cooled to room temperature.

The release results of a final product were as follows:

TABLE 18

Scaled-up results of formulation in Example 7

| Inspection items | Test standards | Test data | Item conclusion |
|---|---|---|---|
| Description | The product is a transparent or semi-transparent gel | Transparent gel | Pass |
| Related substances | Single impurity ≤ 0.2%; Imp-F ≤ 3.0%; Total impurities ≤ 3.0%. | Single impurity < LOQ Imp-F: 0.09% Total impurities: 0.09% | Pass |
| pH | 3.0~4.5 | 3.65 | Pass |
| Benzoic acid content | It should be 80.0%-120.0% of the labeled content. | 99.5% | Pass |
| Content determination | The content of diltiazem hydrochloride should be 93.0%-107.0% of the labeled content | 101.4% | Pass |

The following provides an evaluation of the safety of the formulation of the present patent.

(1) Rabbit One-Week Irritation Test

The rabbit one-week irritation test was conducted on 10 rabbits by using the formulation of Example 7. The rabbits were divided into two groups, a normal skin group plus a damaged skin group. Each group was continuously administered 3 times a day for one week, about 1 g (2.5 cm) each time. The skin observation scoring was shown in Table 19, and the irritation evaluation results were shown in Table 20.

TABLE 19

Skin observation scoring

| Skin reaction evaluation | Score |
|---|---|
| Erythema (redness) and eschar formation | |
| No erythema | 0 |
| Mild erythema | 1 |
| Clearly visible erythema | 2 |
| Moderate erythema | 3 |
| Severe erythema | 4 |
| Severe erythema to mild eschar formation | 5 |
| Edema | |
| No edema | 0 |
| Very slight edema | 1 |
| Mild edema (obvious bulging, well-defined region) | 2 |
| Moderate edema (skin bulging of about 1.0 mm) | 3 |
| Severe edema (skin bulging of greater than 1.0 mm) | 4 |

TABLE 20

Incidence and severity of rabbit skin irritation

| | Normal skin | Damaged skin |
|---|---|---|
| Erythema (redness) and eschar formation (scoring) | | |
| No erythema | 5 | 5 |
| Mild erythema | 0 | 0 |
| Clearly visible erythema | 0 | 0 |
| Moderate erythema | 0 | 0 |
| Severe erythema | 0 | 0 |
| Severe erythema to mild eschar formation | 0 | 0 |
| Edema (scoring) | | |
| No edema | 5 | 5 |
| Very slight edema | 0 | 0 |
| Mild edema (obvious bulging, well-defined region) | 0 | 0 |
| Moderate edema (skin bulging of about 1.0 mm) | 0 | 0 |
| Severe edema (skin bulging of greater than 1.0 mm) | 0 | 0 |

The results showed that no skin erythema and edema was observed in all groups within 1 week after administration. It could be determined that this product was non-irritating within 1 week.

(2) Guinea Pig Skin 2-Week Allergy Test

In this test, guinea pigs were used as the test system to detect, by the Buehler method, the skin allergic reaction caused by 2.0% diltiazem hydrochloride gel, with dinitrochlorobenzene (DNCB) as a positive control. A total of 20 guinea pigs were randomized into 4 groups, including a positive control group, a negative control group, a test article dosage group and a blank solvent group, with 5 animals in each group. 3 sensitizations and 2 exication were carried out in a sensitization contact stage. Rash and edema at the administration site were observed.

TABLE 21

Observations of Guinea pig skin after first excitation
Number of animals with different scoring

| Group | Quan-tity | Time point | Erythema | | | | | | Edema | | | | | Sensi-tization rate (%) |
|---|---|---|---|---|---|---|---|---|---|---|---|---|---|---|
| | | | 0 | 1 | 2 | 3 | 4 | 5 | 0 | 1 | 2 | 3 | 4 | |
| Positive control | 5 | 24 h | 2 | 3 | 0 | 0 | 0 | 0 | 3 | 2 | 0 | 0 | 0 | 60% |
| | | 48 h | 2 | 3 | 0 | 0 | 0 | 0 | 4 | 1 | 0 | 0 | 0 | 60% |
| Negative control | 5 | 24 h | 5 | 0 | 0 | 0 | 0 | 0 | 5 | 0 | 0 | 0 | 0 | 0 |
| | | 48 h | 5 | 0 | 0 | 0 | 0 | 0 | 5 | 0 | 0 | 0 | 0 | 0 |
| Test article group | 5 | 24 h | 5 | 0 | 0 | 0 | 0 | 0 | 5 | 0 | 0 | 0 | 0 | 0 |
| | | 48 h | 5 | 0 | 0 | 0 | 0 | 0 | 5 | 0 | 0 | 0 | 0 | 0 |
| Blank solvent group | 5 | 24 h | 5 | 0 | 0 | 0 | 0 | 0 | 5 | 0 | 0 | 0 | 0 | 0 |
| | | 48 h | 5 | 0 | 0 | 0 | 0 | 0 | 5 | 0 | 0 | 0 | 0 | 0 |

Note:
The incidence refers to the percentage of occurrence of allergic reactions to animals after excitation (within 24 h or 48 h).

TABLE 22

Observations of re-excited skin
Number of animals with different scoring

| Group | Quan-tity | Time point | Erythema | | | | | | Edema | | | | | Sensi-tization rate (%) |
|---|---|---|---|---|---|---|---|---|---|---|---|---|---|---|
| | | | 0 | 1 | 2 | 3 | 4 | 5 | 0 | 1 | 2 | 3 | 4 | |
| Positive control | 5 | 24 h | 1 | 4 | 0 | 0 | 0 | 0 | 5 | 0 | 0 | 0 | 0 | 80% |
| | | 48 h | 1 | 4 | 0 | 0 | 0 | 0 | 3 | 2 | 0 | 0 | 0 | 80% |
| Negative control | 5 | 24 h | 5 | 0 | 0 | 0 | 0 | 0 | 5 | 0 | 0 | 0 | 0 | 0 |
| | | 48 h | 5 | 0 | 0 | 0 | 0 | 0 | 5 | 0 | 0 | 0 | 0 | 0 |
| Test article group | 5 | 24 h | 5 | 0 | 0 | 0 | 0 | 0 | 5 | 0 | 0 | 0 | 0 | 0 |
| | | 48 h | 5 | 0 | 0 | 0 | 0 | 0 | 5 | 0 | 0 | 0 | 0 | 0 |
| Blank solvent group | 5 | 24 h | 5 | 0 | 0 | 0 | 0 | 0 | 5 | 0 | 0 | 0 | 0 | 0 |
| | | 48 h | 5 | 0 | 0 | 0 | 0 | 0 | 5 | 0 | 0 | 0 | 0 | 0 |

The results showed that no potential allergenicity was observed after the administration of 2.0% diltiazem hydrochloride gel and a blank solvent to guinea pigs. In addition, the negative control group showed a negative result, and the positive control group developed sensitization symptoms, indicating that the test system was valid.

Example 8

TABLE 23

Compositions of formulations with the concentrations of 1% and 4%

| Compositions of formulations | 1% | 4% |
|---|---|---|
| Diltiazem hydrochloride | 1 g | 4 g |
| Propylene glycol | 90.50 g | 87.50 g |
| Benzoic acid | 0.5 g | 0.5 g |
| Hydroxypropyl cellulose | 8 g | 8 g |
| Total weight | 100 g | 100 g |

The preparation method was shown in Method of Example 7.

TABLE 24

3-month stability evaluation results for the concentrations of 1% and 4%

| Storage condition and time | 1% | 4% |
|---|---|---|
| 0 day | Single impurity: <LOQ<br>Imp-F: 0.07%<br>Total impurities: 0.07% | Single impurity: <LOQ<br>Imp-F: 0.06%<br>Total impurities: 0.06% |
| Cold storage (2-8° C.), 3M | Single impurity: <LOQ<br>Imp-F: 0.16%<br>Total impurities: 0.16% | Single impurity: <LOQ<br>Imp-F: 0.13%<br>Total impurities: 0.13% |
| 25° C./60% RH, 3M (room temperature) | Single impurity: 0.06%<br>Imp-F: 0.67%<br>Total impurities: 0.73% | Single impurity: <LOQ<br>Imp-F: 0.70%<br>Total impurities: 0.70% |

The stability data met the internal control requirements of the present application.

Example 9

After the content of propylene glycol in the preparation method in Example 7 was changed to 35%, the stability data met the internal control requirements of the present application.

Example 10

After the content of propylene glycol in the preparation method in Example 7 was changed to 70%, the stability data met the internal control requirements of the present application.

Example 11

TABLE 25

Formulations in other examples

| Compositions of formulations | 1% | 1% | 4% | 4% |
|---|---|---|---|---|
| Diltiazem hydrochloride | 1 g | 1 g | 4 g | 4 g |
| Propylene glycol | 91.75 g | 89.25 g | 88.75 g | 86.25 g |
| Benzoic acid | 0.25 g | 0.75 g | 0.25 g | 0.75 g |
| Hydroxypropyl cellulose | 7 g | 9 g | 7 g | 9 g |
| Total weight | 100 g | 100 g | 100 g | 100 g |

The preparation method could be found in Method of Example 7, and the stability data met the internal control requirements of the present application.

The invention claimed is:

1. A pharmaceutical composition of diltiazem hydrochloride, which is in the form of a gel and consists of diltiazem hydrochloride and excipients, wherein the excipients comprise propylene glycol, benzoic acid, and a gel matrix, wherein the gel matrix comprises one or both of povidone and hydroxypropyl cellulose, wherein, based on percentage by weight in the composition, the diltiazem hydrochloride accounts for 1%-5%, the benzoic acid accounts for 0.1%-5.0%, the gel matrix accounts for 5%-10%, and the balance is propylene glycol.

2. The pharmaceutical composition of diltiazem hydrochloride according to claim 1, wherein the benzoic acid accounts for 0.1%-3.0%, and the gel matrix accounts for 5.0%-9.0%.

3. The pharmaceutical composition of diltiazem hydrochloride according to claim 1, wherein the diltiazem hydrochloride accounts for 1%-4%, the benzoic acid accounts for 0.1%-2.0%, and the gel matrix accounts for 7.0%-9.0%.

4. The pharmaceutical composition of diltiazem hydrochloride according to claim 1, wherein the diltiazem hydrochloride accounts for 1%-4%, the benzoic acid accounts for 0.1%-1.0%, and the gel matrix accounts for 7.0%-9.0%.

5. The pharmaceutical composition of diltiazem hydrochloride according to claim 1, wherein the diltiazem hydrochloride accounts for 1%-4%, the benzoic acid accounts for 0.25%-0.75%, and the gel matrix accounts for 7.0%-9.0%.

6. The pharmaceutical composition of diltiazem hydrochloride according to claim 1, wherein the gel matrix is hydroxypropyl cellulose.

7. The pharmaceutical composition of diltiazem hydrochloride according to claim 1, wherein the diltiazem hydrochloride accounts for 2% or 4% by weight.

8. A method for preparing the pharmaceutical composition of claim 1, comprising the following steps:
   1) mixing propylene glycol accounting for 35%-70% of a prescribed amount with a gel matrix, heating and stirring a resulting mixture for emulsification to obtain a matrix A;
   2) mixing a prescribed amount of benzoic acid with the balance of the propylene glycol, and stirring a resulting mixture to obtain a solution B;
   3) adding a prescribed amount of diltiazem hydrochloride to the solution B, stirring and heating a resulting mixture for dissolution to obtain a solution C; and
   4) adding the solution C to the matrix A for overall mixing in a homogeneous and uniform manner, and cooling a resulting mixture to room temperature to obtain the pharmaceutical composition.

9. A method of treating anal fissures and/or postoperative pain of anal fissures or hemorrhoids, comprising administering to a patient in need thereof the pharmaceutical composition of claim 1.

* * * * *